United States Patent
Park et al.

(10) Patent No.: US 8,172,858 B2
(45) Date of Patent: May 8, 2012

(54) SUTURE DEVICE FOR SURGICAL OPERATION

(75) Inventors: Hyun-Chul Park, Pohang-si (KR);
Young-Ho Jang, Daegu (KR);
Kyeng-Ho Hwang, Anyang-si (KR);
Hun-Kee Lee, Pohang-si (KR)

(73) Assignee: Postech Academy-Industry Foundation, Nam-Ku, Kyungsangbuk-Do Pohang (KR)

( * ) Notice: Subject to any disclaimer, the term of this patent is extended or adjusted under 35 U.S.C. 154(b) by 310 days.

(21) Appl. No.: 12/555,047

(22) Filed: Sep. 8, 2009

(65) Prior Publication Data
US 2010/0063519 A1    Mar. 11, 2010

(30) Foreign Application Priority Data
Sep. 11, 2008  (KR) .................. 10-2008-0089708

(51) Int. Cl.
*A61B 17/10* (2006.01)
*A61B 17/04* (2006.01)
(52) U.S. Cl. ...................... 606/139; 606/144
(58) Field of Classification Search ............ 606/139, 606/144–147
See application file for complete search history.

(56) References Cited

U.S. PATENT DOCUMENTS

| | | | | |
|---|---|---|---|---|
| 4,437,465 | A | * | 3/1984 | Nomoto et al. ............... 606/144 |
| 5,766,186 | A | | 6/1998 | Faraz et al. |
| 2010/0145364 | A1 | * | 6/2010 | Keren et al. .................. 606/144 |

FOREIGN PATENT DOCUMENTS

| | | |
|---|---|---|
| JP | 56-089246 | 7/1981 |
| JP | 57-152113 | 9/1982 |
| KR | 10-2006-0013299 | 2/2006 |

* cited by examiner

*Primary Examiner* — Tuan Nguyen
(74) *Attorney, Agent, or Firm* — Lexyoume IP Group, PLLC.

(57) ABSTRACT

The described technology relates to a suture device for a surgical operation that makes it easy to suture a wound or an incision. A suture device for a surgical operation includes: a suture needle that is curved with a needle eye at one end to be threaded with a first suture, and swings at an incision; a holder that supplies a second suture, rotates in one direction, and stops, corresponding to the swing of the suture needle to weave the first suture and the second suture and suture the incision; a first rotary member that is connected to a first shaft of the suture needle; a second rotary member that is connected to a second shaft of the holder; and a third rotary member that is provided between the first rotary member and the second rotary member, and connected to a third shaft to transmit torque to the second rotary member.

10 Claims, 9 Drawing Sheets

(a)

(b)

SUTURE DEVICE FOR SURGICAL OPERATION

CROSS-REFERENCE TO RELATED APPLICATION

This application claims priority to and the benefit of Korean Patent Application No. 10-2008-0089708 filed in the Korean Intellectual Property Office on Sep. 11, 2008, the entire content of which is incorporated herein by reference.

BACKGROUND OF THE INVENTION (a) Field of the Invention

The present invention relates to a suture device for a surgical operation. More particularly, the present invention relates to a suture device for a surgical operation that makes it easy to suture a wound or an incision and enables uniform sutures.

(b) Description of the Related Art

Suture needles and sutures are used for suturing a wound or an incision for a surgical operation. Referring to FIG. 10, a surgical operation is performed by threading a suture needle 1 with a suture 2, holding the suture needle 1 with a holder (not shown), inserting the suture needle 1 into a wound or an incision 3 and suturing it (a to d), and then fixing the suture 2(e).

Referring to FIG. 11, a process of fixing the suture 2 is performed by winding one end of the suture 2 with a pair of forceps 4(a), gripping the other end with the pair of forceps (4)(b), firstly fixing the suture 2 by passing the other end through a ring formed by the wound suture 2(c), and then again winding one end of the suture 2 while holding the other end with the pair of forceps 4(d), and then secondly fixing the suture 2 by passing the other end through a ring formed by the wound suture 2(e).

As described above, since several processes are required to suture the wound and the incision 3, the time for suturing is long and uniformity of the suturing is deteriorated. Further, the suturing requires a high degree of skill.

The above information disclosed in this Background section is only for enhancement of understanding of the background of the invention and therefore it may contain information that does not form the prior art that is already known in this country to a person of ordinary skill in the art.

SUMMARY OF THE INVENTION

The described technology relates to a suture device for a surgical operation that makes it easy to suture a wound or an incision.

Further, the described technology relates to a suture device for a surgical operation that makes it possible to achieve uniform suturing, without a large influence by suturing skill.

A suture device for a surgical operation according to an exemplary embodiment of the described technology may include: a suture needle that is curved with a needle eye at one end to be threaded with a first suture, and that swings at an incision; a holder that supplies a second suture, rotates in one direction, and stops, corresponding to the swing of the suture needle to weave the first suture and the second suture to suture the incision; a first rotary member that is connected to a first shaft of the suture needle; a second rotary member that is connected to a second shaft of the holder; and a third rotary member that is provided between the first rotary member and the second rotary member, and is connected to a third shaft to transmit torque to the second rotary member from the first rotary member.

The suture device for a surgical operation according to an exemplary embodiment of the described technology further includes a swing operation unit that swings the suture needle, and the swing operation unit may include a rack that swings the first rotary member while straightly reciprocating.

The swing operation unit may include a pinion gear engaged with the rack, a first gear fitted on a fourth shaft supporting the pinion gear and having a larger diameter than the pinion gear, and a second gear engaged with the first gear, having a smaller diameter than the first gear, and fitted on the first shaft.

The suture device for a surgical operation according to an exemplary embodiment of the described technology may include a lower body that supports the first shaft, the second shaft, the third shaft, and the fourth shaft, and an upper body that is connected by a hinge to the lower body at a side of the second shaft and connected to the rack by a link member at the opposite side to the hinge.

The suture needle may include a first hub fitted on the first shaft, a first body that is formed in a curve shape spaced apart from the first hub in a first diameter direction, and a first connecting member that connects the first body to the first hub, in the first diameter direction. The first body may be formed in a three-quarter circular shape.

The holder may include a second hub fitted on the second shaft, a second body that is formed in a curve shape spaced apart from the second hub in a second diameter direction, and a second connecting member that connects the second body to the second hub, in the second diameter direction. The second body may be formed in a semicircular shape.

The end of the first body of the suture needle and the end of the second body of the holder may cross each other at one end of the third shaft, and may be spaced apart from each other in the longitudinal direction of the third shaft.

A first diameter of the first body of the suture needle may be larger than a second diameter of the second body of the holder.

The second rotary member and the second shaft may be connected by a ratchet.

The first rotary member, the second rotary member, and the third rotary member may be gears.

As described above, according to an exemplary embodiment of the described technology, the curved suture needle swings at the incision and the curved holder rotates and stops, corresponding to the swing of the suture needle, such that the first suture of the suture needle and the second suture of the holder are woven. Therefore, it is possible to easily suture the incision.

Further, the swing operation unit is further provided, such that as the swing operation unit swings the suture needle, it is possible to achieve uniform suturing, without a large influence by suturing skill.

DETAILED DESCRIPTION OF THE EMBODIMENTS

Figure 1:
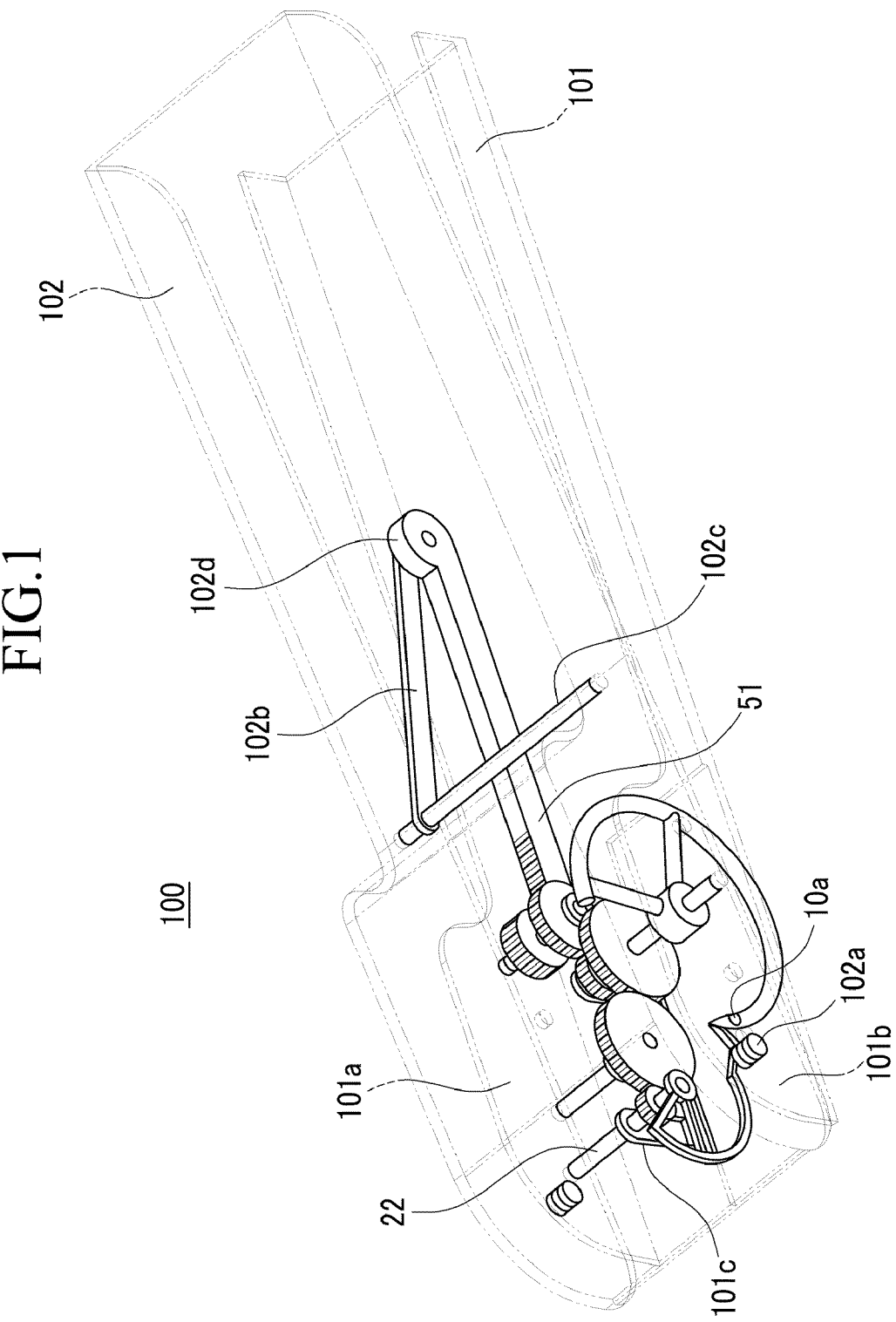
FIG. 1 is a perspective view of a suture device for a surgical operation according to an exemplary embodiment of the present invention.

The present invention will be described more fully hereinafter with reference to the accompanying drawings, in which exemplary embodiments of the invention are shown. As those skilled in the art would realize, the described embodiments may be modified in various different ways, all without departing from the spirit or scope of the present invention. The drawings and description are to be regarded as illustrative in nature and not restrictive. Like reference numerals designate like elements throughout the specification.

FIG. 1 is a perspective view of a suture device for a surgical operation according to an exemplary embodiment of the present invention. Referring to FIG. 1, a suture device 100 for a surgical operation according to an exemplary embodiment includes a suture needle 10, a holder 20, a first rotary member 11, a second rotary member 21, and a third rotary member 30.

The suture device for a surgical operation 100 is configured to allow the suture needle 10 to swing and the holder 20 to rotate only in one direction corresponding to a swing of the suture needle 10, and not to rotate in the opposite direction.

Figure 2:
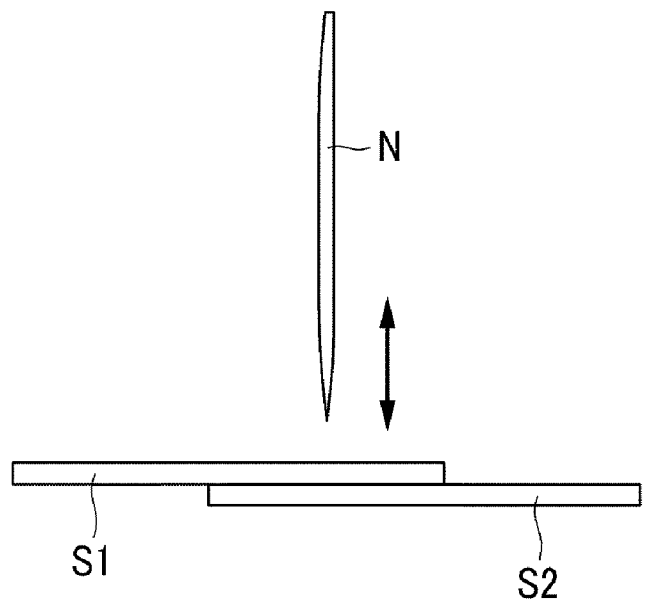
FIG. 2 is a schematic view illustrating sewing by a sewing machine.
Figure 3:
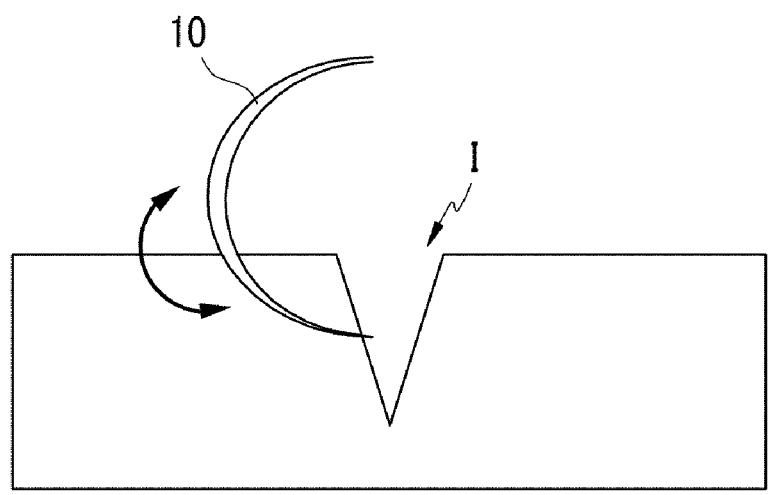
FIG. 3 is a schematic view illustrating suturing by the suture device for a surgical operation of FIG. 1.

FIG. 2 is a schematic view illustrating sewing by a sewing machine and FIG. 3 is a schematic view illustrating suturing by the suture device for a surgical operation of FIG. 1. First, the present exemplary embodiment is described, comparing FIG. 2 with FIG. 3, to help understanding of the present exemplary embodiment.

In general, a sewing machine sews two pieces of overlapped cloth S1 and S2 by reciprocating a needle N up and down through the pieces of cloth S1 and S2.

It is possible to consider an exemplary embodiment of the present invention from the concept illustrated in FIG. 2. FIG. 3 illustrates a suturing concept that is applied to the suture device for a surgical operation 100 according to an exemplary embodiment of the present invention.

According to the suturing concept of the present exemplary embodiment, an incision (I) is sutured by swinging the suture needle 10 through a wound or incision (I) (hereafter referred to as an incision).

Figure 4:
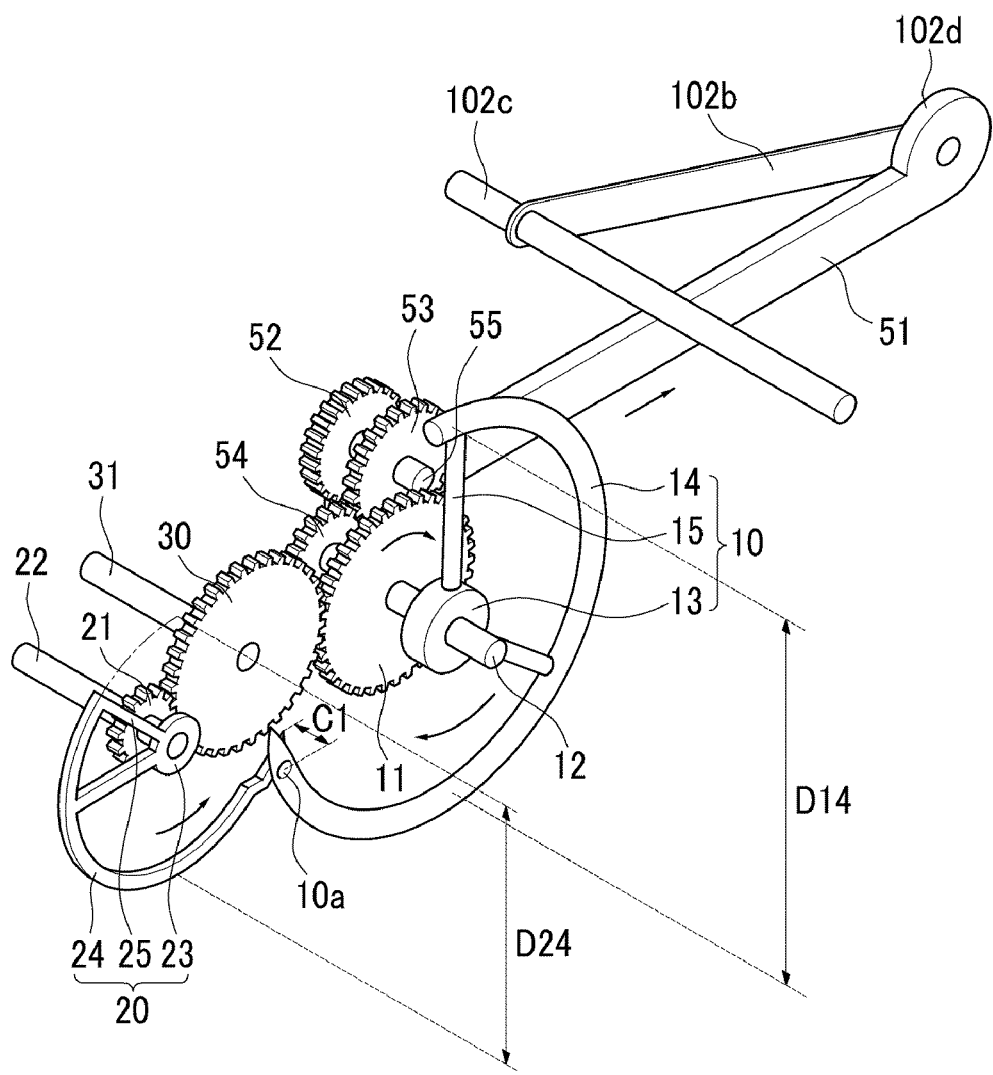
FIG. 4 is a front perspective view of main components of the suture device for a surgical operation of FIG. 1.
Figure 5:
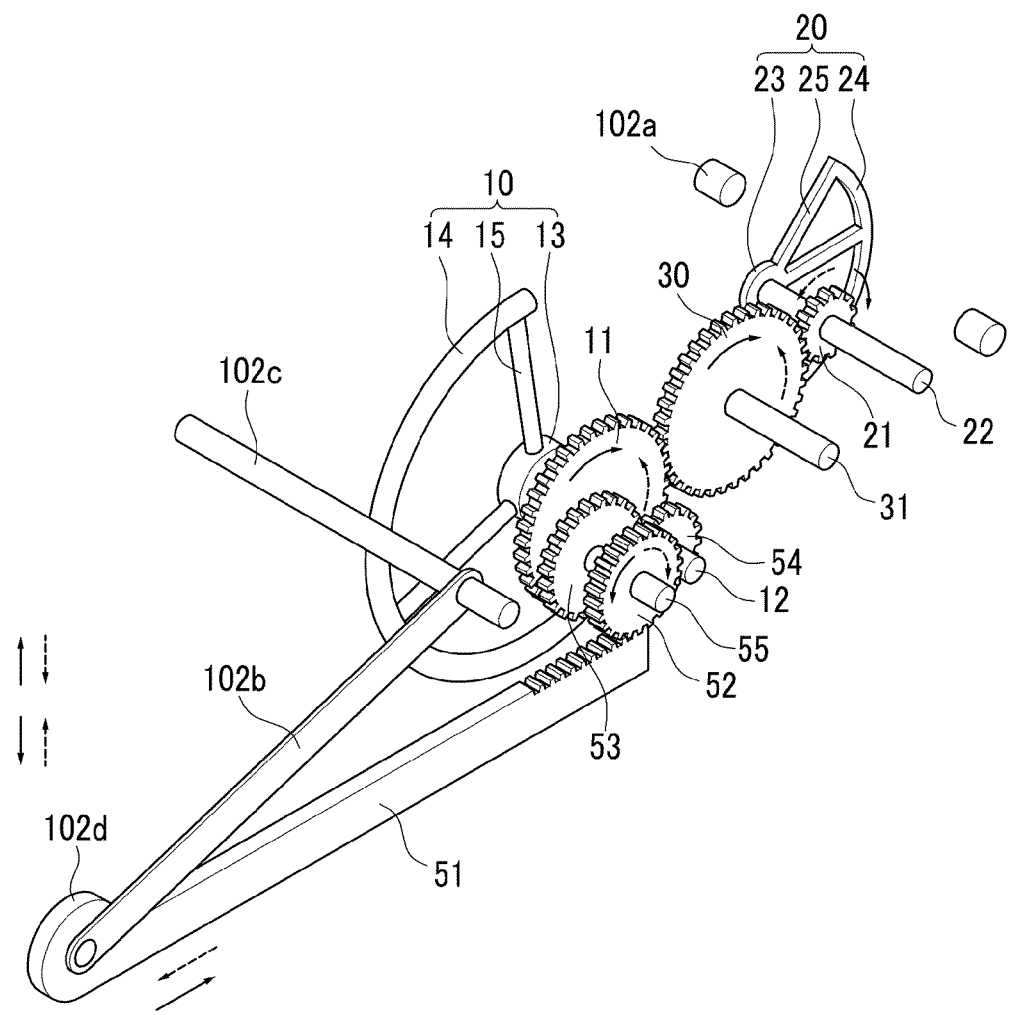
FIG. 5 is a rear perspective view of the main components of the suture device for a surgical operation of FIG. 1.

FIG. 4 is a front perspective view of main components of the suture device for a surgical operation of FIG. 1, and FIG. 5 is a rear perspective view of the main components of the suture device for a surgical operation of FIG. 1.

Referring to FIG. 1, FIG. 4, and FIG. 5, the suture needle 10 is curved to penetrate the incision (I) while swinging, and has a needle eye 10a at one end. A first suture 41 (see FIG. 7) threaded in the needle eye 10a is supplied to the incision (I) by the swing operation of the suture needle 10.

The holder 20 supplies a second suture 42 (see FIG. 7), corresponding to the first suture 41 of the suture needle 10. The holder 20 sutures the incision (I) with the first suture 41 and the second suture 42 by weaving the first suture 41 supplied by the suture needle 10 and the second suture 42 supplied by the holder 20 while rotating in one direction or stopping, corresponding to the swing operation of the suture needle 10.

To weave the first suture 41 with the second suture 42, the suture needle 10 and the holder 20 need to organically operate with respect to time and space. For this purpose, an exemplary embodiment allows the holder 20 to rotate in one direction and stop by transmitting torque that swings the suture needle 10 to the holder 20.

For example, the first rotary member 11 is fitted on a first shaft 12 where the suture needle 10 is mounted. The second rotary member 21 is fitted on a second shaft 22 where the holder 20 is mounted. The first shaft 12 and the second shaft 22 are in parallel with each other, and the first rotary member 11 and the second rotary member 21 are also maintained in parallel with each other.

The third rotary member 30 is fitted on a third shaft 31 that is disposed in parallel with the first and second shafts 12 and 22, between the first and second rotary members 11 and 21. Therefore, torque of the first rotary member 11 is transmitted to the second rotary member 21 through the third rotary member 30.

For example, the first, second, and third rotary members 11, 21, and 30 are gears that are engaged to transmit torque.

The suture device 100 for a surgical operation of an exemplary embodiment may further include a swing operation unit to supply torque for swinging the suture needle 10 to the suture needle 10. For example, the swing operation unit may be a rack 51 that straightly reciprocates.

The rack 51 is connected to the first rotary member 11 and rotates the first rotary member 11. The rack may be directly connected to the first rotary member, which is a gear (not shown).

In the present exemplary embodiment, the swing operation unit may further include a pinion gear 52 connected to the rack 51, a first gear 53, and a second gear 54. The rack 51 and the pinion gear 52 convert the straight reciprocating motion of the rack 51 to rotational motion of the pinion gear 52.

The pinion gear 52 is fitted on a fourth shaft 55. The fourth shaft 55 is parallel with the first shaft 12 and disposed at one end of the suture needle 10. The first gear 53 is fitted on the fourth shaft 55 and rotates in the same direction as the pinion gear 52.

The second gear 54 is fitted on the first shaft 12 and engaged with the first gear 53, and rotates in the opposite direction to the first gear 53.

The first gear 53 has a larger diameter than the pinion gear 52 and the second gear 54 has a smaller diameter than the first gear 53, such that the rotational amount of the pinion gear 52 is transmitted to the second gear 54 through the first gear 53, thereby increasing the rotational amount of the second gear 54.

Therefore, the straight reciprocating motion of the rack 51 rotates the pinion gear 52 clockwise and counterclockwise, the rotation of the pinion gear 52 rotates the second gear 54 and the first shaft 12 clockwise and counterclockwise through the fourth shaft 55 and the first gear 53, and the rotation of the first shaft 12 swings the suture needle 10.

Simultaneously, the first rotary member 11 fitted on the first shaft 12 rotates the second rotary member 21 through the third rotary member 30. The second rotary member 21 rotates second shaft 22 and the holder 20 in one direction through a ratchet 60 (see FIG. 6), and stops them in the opposite direction.

Figure 6:
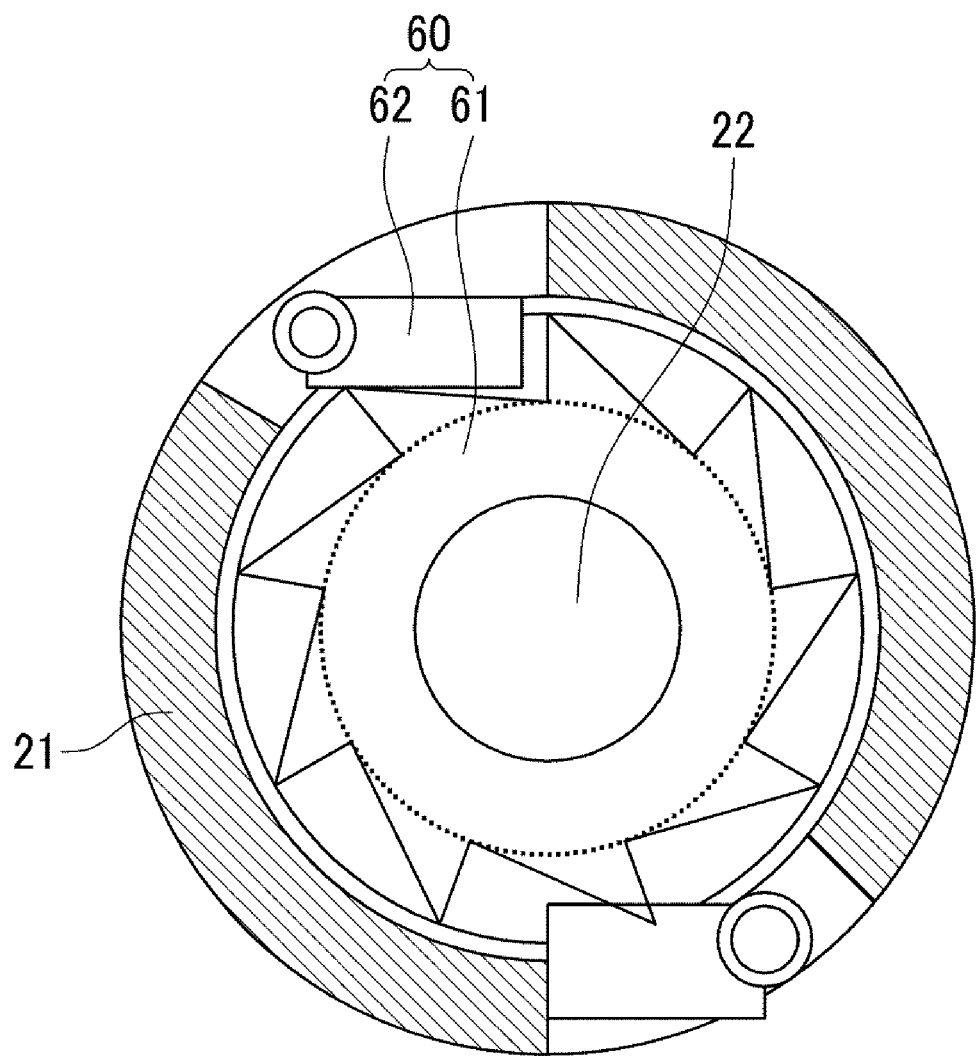
FIG. 6 is a schematic diagram of a ratchet.

FIG. 6 is a schematic diagram of the ratchet. Referring to FIG. 6, the ratchet 60 is disposed between the second shaft 22 equipped with the holder 20 and the second rotary member 21. The ratchet 60 includes an inner ring 61 and a locking member 62.

The inner ring 61 is fitted on the second shaft 22 and integrally rotates or stops with the second shaft 22, and the locking member 62 is fixed to the second rotary member 21 and elastically contacts teeth of the inner ring 61.

Therefore, the second rotary member 21 idles counterclockwise. In this state, the second shaft 22 and the inner ring 61 are in stop mode and the holder 20 mounted on the second shaft 22 is also in stop mode. When the suture needle 10 is inserted into the incision (I), the holder 20 is in stop mode.

As the second rotary member 21 rotates clockwise, the locking member 62 is engaged with the teeth of the inner ring 61, such that the second rotary member 21, the second shaft 22, and the holder 20 integrally rotate clockwise. As the suture needle 10 is removed from the incision (I), the holder 20 rotates clockwise.

Meanwhile, referring again to FIG. 1, the suture device 100 for a surgical operation of an exemplary embodiment includes a lower body 101 and an upper body 102. The lower body 101 is provided with side walls 101a and 101b or a specific bracket 101c, such that it rotatably supports the first shaft 12, the second shaft 22, the third shaft 31, and the fourth shaft 55. Further, the lower body 101 functions as a pressing plate (see FIG. 7) which presses the incision (I), when the suture device 100 for a surgical operation is operated.

The upper body 102 is connected to the lower body 101 by a hinge 102a at one side of the second shaft 22, and is connected to a link member 102b by the rack 51 at the opposite side to the hinge 102a. The link member 102b is connected to a shaft 102c mounted in the upper body 102.

A torsion spring (not shown) may be disposed at a joint 102d of the link member 102b and the rack 51. When holding the lower body 101 and the upper body 102 together, the torsion spring is elastically distorted, and returns when releasing them.

The restoring force of the torsion spring moves the upper body 102 away from the lower body 101 at the joint 102d which is opposite to the hinge 102a, and maintains an open position.

In more detail with reference to FIG. 4 and FIG. 5, the suture needle 10 includes a first hub 13 fitted on the first shaft 12, a first body 14, and a first connecting member 15.

The first body 14 is formed in a curve shape radially space apart from the first hub 13, and has a needle eye 10a at one end to be threaded with the first suture 41.

The first connecting member 15 connects the first body 14 to the first hub 13 in the diameter direction. One or more first connecting members 15 are provided to strengthen the overall structure of the suture needle 10.

The holder 20 has a similar shape to that of the suture needle 10 to correspond to the suture needle 10. The holder 20 includes a second hub 23 fitted on the second shaft 22, a second body 24, and a second connecting member 25.

The second body 24 is formed in a curve shape spaced apart in the diameter direction from the second hub 23, and has a receiving portion 26 (see FIG. 7) at one end facing the needle eye 10a to receive the first suture 41 from the needle eye 10a. When the second body 24 rotates, the receiving portion 26 receives the first suture 41 and weaves the first suture 41 and the second suture 42 by the next additional rotation.

The second connecting member 25 connects the second body 24 to the second hub 23 in the diameter direction. One or more second connecting members 25 are provided to strengthen the overall structure of the holder 20.

The suture needle 10 and the holder 20 are disposed to face each other across the third shaft 31. When the suture needle 10 and the holder 20 interact, the end of the first body 14 and the end of the second body 25 cross each other substantially on an extension line of the third shaft 31 to weave the first suture 41 and the second suture 42, and are disposed to be spaced apart from each other by a distance C1 in the longitudinal direction of the third shaft 31. Therefore, it is possible to weave the first suture 41 and the second suture 42 without interference from the ends of the bodies 14 and 24.

Meanwhile, the first diameter D14 of the first body 14 of the suture needle 10 may be larger than the second diameter D24 of the second body 24 of the holder 20. Further, the first body 14 may be formed in a three-quarter circular shape to penetrate the incision (I) and the second body 24 may be formed in a semicircular shape to weave the first suture 41 and the second suture 42.

In the first body 14 and the second body 24 of the suture needle 10 and the holder 20, the diameters and the lengths of the curves can be variously set in a range that enables 360 degrees rotation of the holder 20 while the suture needle 10 makes one swing.

Figure 7:
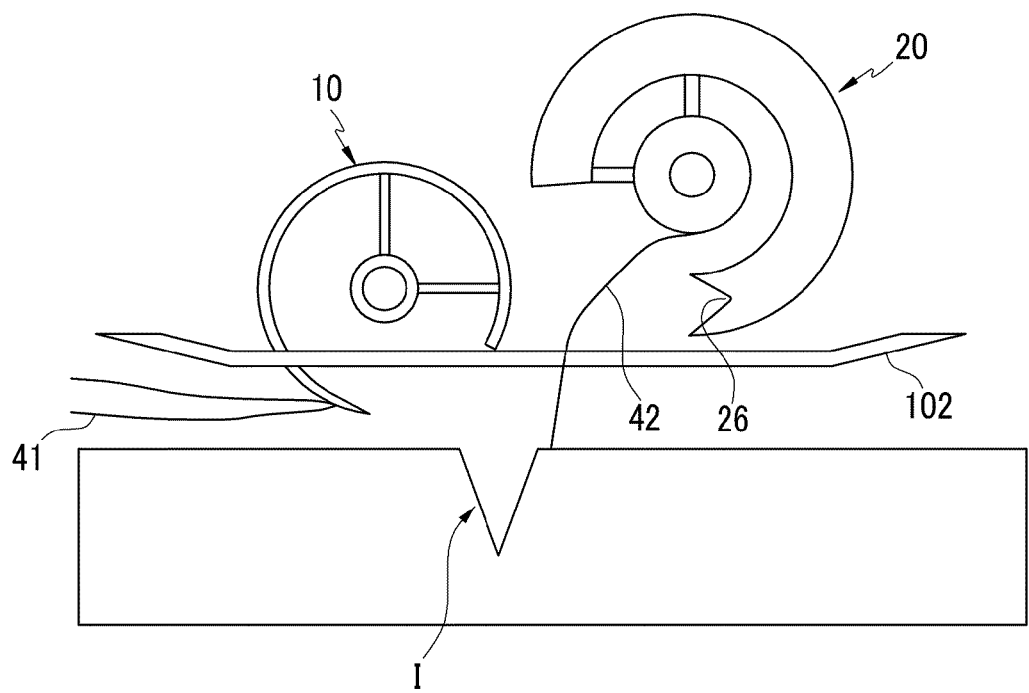
FIG. 7 is a schematic view illustrating suturing of the suture device for a surgical operation of FIG. 1.
Figure 8:
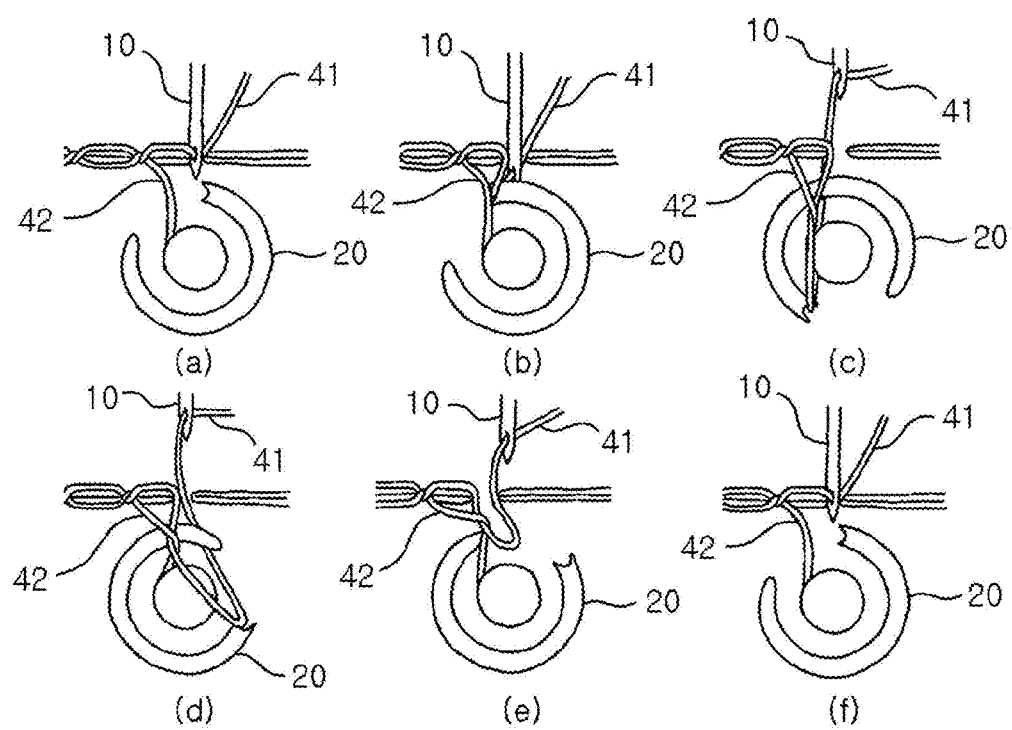
FIG. 8 is a flowchart illustrating a suturing process by a suture needle in the suture device for a surgical operation of FIG. 1.

FIG. 7 is a schematic view illustrating suturing of the suture device for a surgical operation of FIG. 1, and FIG. 8 is a flowchart illustrating a suturing process by a suture needle in the suture device for a surgical operation of FIG. 1. To ease understanding, the suture needle 10 that performs swing operation is illustrated in a straight line shape in FIG. 8 for straight line back-and-forth operation First, description is provided with reference to FIG. 5. As the lower body 101 of the suture device 100 for a surgical operation is placed on the incision (I) and then lower body 101 and the upper body 102 are clenched, the lower body 101 and the upper body 102 come closer at the side opposite to the hinge 102a, the rack 51 moves backward by the link member 102b connected to the upper body 102, and the pinion gear 52 rotates clockwise.

In this operation, the suture needle 10 rotates counterclockwise through the first gear 53, the second gear 54, the first rotary member 11, and the first shaft 12. The suture needle 10, as shown in FIG. 7 and (a) and (b) of FIG. 8, moves into the incision (I).

In this operation, the clockwise torque that is transmitted from the first rotary member 11 fitted on the first shaft 12 to the third rotary member 30 fitted on the third shaft 31 is transmitted to the second rotary member 21. As show in FIG. 7 and (a) and (b) of FIG. 8, the second rotary member 21 idles counterclockwise by the ratchet 60. Accordingly, torque is blocked by the ratchet 60, such that the second shaft 22 and the holder 20 fitted thereon is maintained in the stopped position.

On the contrary, as the lower body 101 and the upper body 102 of the suture device 100 for a surgical operation that have been clenched are released, the lower body 101 and the upper body 102 move away from each other, the rack 51 is moved forward by the link member 102b connected to the upper body 102, and the pinion gear 52 rotates counterclockwise.

In this operation, the suture needle 10 rotates clockwise through the first gear 53, the second gear 54, the first rotary member 11, and the first shaft 12. The suture needle 10, as shown in FIG. 7 and (c), (d), and (e) of FIG. 8, penetrates the incision (I) and returns out.

In this operation, the counterclockwise torque that is transmitted from the first rotary member 11 fitted on the first shaft 12 to the third rotary member 30 fitted on the third shaft 31 is transmitted to the second rotary member 21. As shown in FIG. 7 and (b), (c), (d), and (e) of FIG. 8, the second rotary member 21 holds and weaves the first suture 41 with the second suture while rotating clockwise by the ratchet 60.

That is, when the needle eye 10a of the suture needle 10 meets the receiving portion 26 of the holder 20, the first suture 41 coming out of the suture needle 10 is delivered to the receiving portion 26 of the holder 20. The first suture 41 delivered to the receiving portion 26 is woven with the second suture 42 coming out of the holder 20. The first suture 41 returns to the suture needle 10 by attraction generated when the suture needle 10 returns to its original position.

As the lower body 101 and the upper body 102 are clenched, the suture needle 10 and the holder 20 are positioned as in (a) of FIG. 8 for the next suture.

Figure 9:
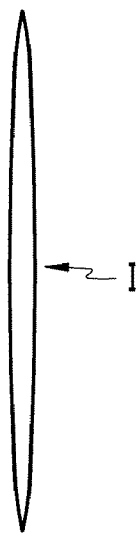
FIG. 9 is a view showing a sutured state by the suture device for a surgical operation of FIG. 1.
Figure 9:
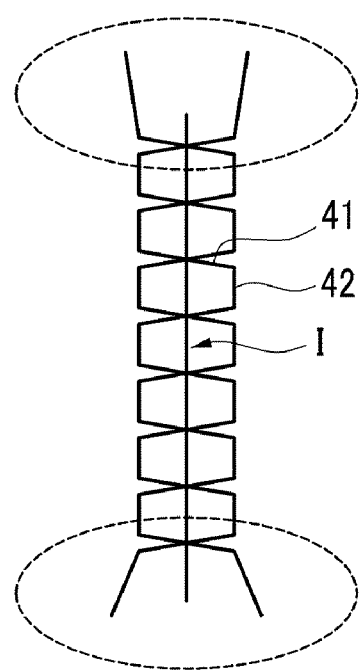
Figure 10:
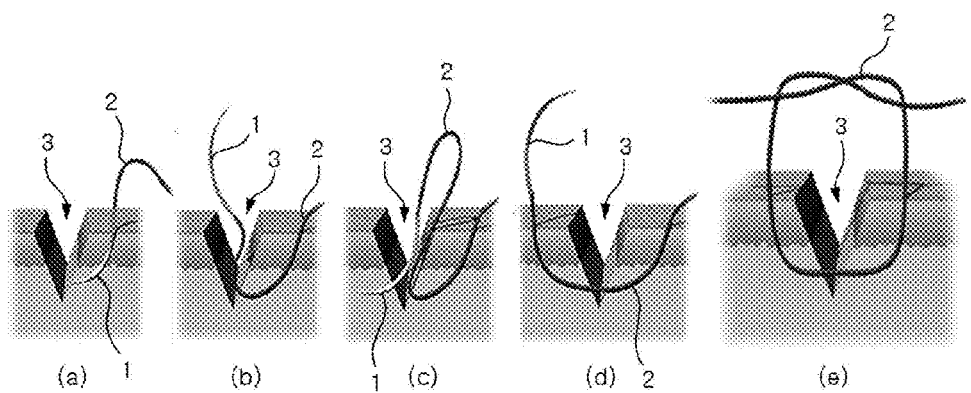
FIG. 10 is a schematic diagram illustrating a suturing process according to the conventional art.
Figure 11:
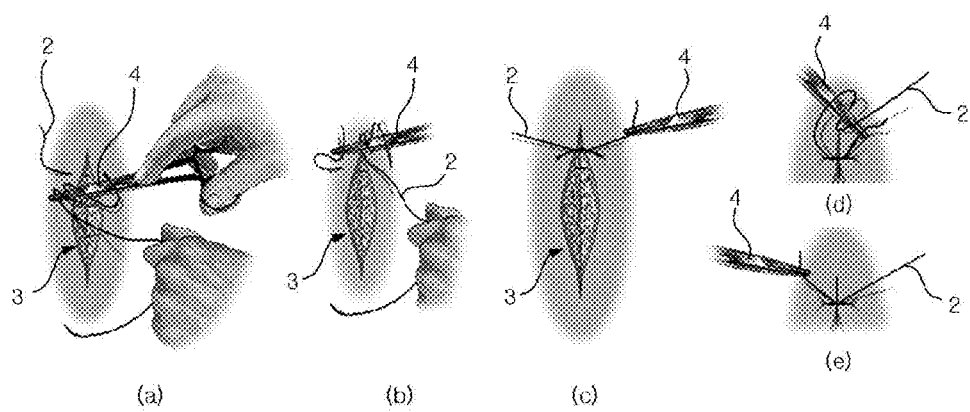
FIG. 11 is a schematic diagram illustrating a process of fixing a suture of FIG. 10.

FIG. 9 is a view showing a sutured state by the suture device for a surgical operation of FIG. 1. Referring to FIG. 9, the incision (I) shown in (a) of FIG. 9 is sutured into the state shown in (b) of FIG. 9. That is, the first and second sutures 41 and 42 are disposed at both sides of the incision line of the incision (I) to perform uniform suturing in the longitudinal direction of the incision (I), thereby reducing side effects at the incision (I).

To achieve uniform suturing as described above, the suture device 100 for a surgical operation according to an exemplary embodiment does not require high skill, thereby reducing a burden of the suturing of the incision (I).

While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims.

What is claimed is:

1. A suture device for a surgical operation, comprising:
  a suture needle that is curved with a needle eye at one end to be threaded with a first suture and supply the first suture, wherein the suture needle is configured to swing at an incision;
  a holder that supplies a second suture, rotates in one direction, and stops, corresponding to the swing of the suture needle to weave the first suture and the second suture to suture the incision;
  a first rotary member that is connected to a first shaft of the suture needle;
  a second rotary member that is connected to a second shaft of the holder;
  a third rotary member that is provided between the first rotary member and the second rotary member, and is connected to a third shaft to transmit torque to the second rotary member; and
  a swing operation unit that swing the suture needle, wherein the swing operation unit includes
  a rack that swings the first rotary member while straightly reciprocating,
  a pinion gear engaged with the rack,
  a first gear fitted on a fourth shaft supporting the pinion gear and having a larger diameter than the pinion gear and
  a second gear engaged with the first gear, having a smaller diameter than the first gear, and fitted on the first shaft.

2. The suture device for a surgical operation of claim 1, comprising:
  a lower body that supports the first shaft, the second shaft, the third shaft, and the fourth shaft; and
  an upper body that is connected by a hinge to the lower body at a side of the second shaft and connected to the rack by a link member at the opposite side to the hinge.

3. The suture device for a surgical operation of claim 1, wherein
  the suture needle comprises:
  a first hub fitted on the first shaft;
  a first body that is formed in a curve shape spaced apart from the first hub in a first diameter direction; and
  a first connecting member that connects the first body to the first hub in the first diameter direction.

4. The suture device for a surgical operation of claim 3, wherein the first body is formed in a three-quarter circular shape.

5. The suture device for a surgical operation of claim 3, wherein
  the holder comprises:
  a second hub fitted on the second shaft;
  a second body that is formed in a curve shape spaced apart from the second hub in a second diameter direction; and
  a second connecting member that connects the second body to the second hub in the second diameter direction.

6. The suture device for a surgical operation of claim 5, wherein the second body is formed in a semicircular shape.

7. The suture device for a surgical operation of claim 5, wherein the end of the first body of the suture needle and the end of the second body of the holder cross each other at one end of the third shaft and are spaced apart from each other in the longitudinal direction of the third shaft.

8. The suture device for a surgical operation of claim 5, wherein a first diameter of the first body of the suture needle is larger than a second diameter of the second body of the holder.

9. The suture device for a surgical operation of claim 5, wherein the second rotary member and the second shaft are connected by a ratchet.

10. The suture device for a surgical operation of claim 1, wherein the first rotary member, the second rotary member, and the third rotary member are gears.

* * * * *